United States Patent [19]

Park et al.

[11] Patent Number: 5,496,726
[45] Date of Patent: Mar. 5, 1996

[54] STREPTOCOCCUS ZOOEPIDEMICUS MEDIUM AND PROCESS FOR PREPARING HYALURONIC ACID

[75] Inventors: Myoung G. Park; Jae D. Jang; Whan K. Kang, all of Daejeon, Rep. of Korea

[73] Assignee: Lucky Limited, Seoul, Rep. of Korea

[21] Appl. No.: 224,895

[22] Filed: Apr. 8, 1994

[30] Foreign Application Priority Data

Apr. 16, 1993 [KR] Rep. of Korea ............ 1993 6423
Apr. 16, 1993 [KR] Rep. of Korea ............ 1993 6424

[51] Int. Cl.⁶ ............ C12N 1/20; C12P 19/04
[52] U.S. Cl. ............ 435/253.4; 435/101; 435/885
[58] Field of Search ............ 435/253.4, 101, 435/885

[56] References Cited

U.S. PATENT DOCUMENTS 4,780,414  10/1988  Nimrod et al. ............ 435/101
4,784,990  11/1988  Nimrod et al. ............ 514/54
5,023,175  6/1991  Hosoya et al. ............ 435/101

FOREIGN PATENT DOCUMENTS 0244757  11/1987  European Pat. Off. ..
0266578  5/1988  European Pat. Off. ..
0363561  4/1990  European Pat. Off. ..

Primary Examiner—Marian C. Knode
Assistant Examiner—Francisco C. Prats
Attorney, Agent, or Firm—Anderson Kill Olick & Oshinsky

[57] ABSTRACT

The present invention relates to a strain of *Streptococcus zooepidemicus* which produces high molecular weight hyaluronic acid; to a process for preparing said hyaluronic acid by employing the strain; and to a medium suitable for the culture of a microorganism producing hyaluronic acid.

3 Claims, 5 Drawing Sheets

STREPTOCOCCUS ZOOEPIDEMICUS MEDIUM AND PROCESS FOR PREPARING HYALURONIC ACID

FIELD OF THE INVENTION

The present invention relates to a novel microorganism capable of producing high molecular weight hyaluronic acid, a process for preparing said hyaluronic acid by employing the microorganism and a medium suitable for culturing the microorganism so as to produce said hyaluronic acid.

DESCRIPTION OF THE PRIOR ART

As well known in the art, hyaluronic acid is a colorless, transparent and highly viscous linear polysaccharide having a molecular weight ranging from 50 kda to 13,000 kda with an unbranched chain of alternating $\beta$-(1,4)-glucuronic acid and $\beta$-(1,3)-N-acetyl glucosamine linkages. Hyaluronic acid and its salts have found numerous usages, e.g., as a vitreous replacement in optical surgery and eye drop formula, and as a moisturizer in cosmetic formulations. Generally, hyaluronic acid is prepared by extracting it from animal tissues or culturing certain microorganisms.

For example, U.S. Pat. No. 4,141,973 (Balaz) describes processes for extracting hyaluronic acid from animal tissues, by way of purifying or removing biopolymer impurities such as chondroitin sulfate and glycosaminoglycan in tissues; and they are not generally regarded as suitable for the mass production thereof due to high cost and low efficiency.

Accordingly, there have been proposed various processes for producing hyaluronic acid by using microorganisms, especially those microorganisms belonging to the genus Streptococcus. The exemplary microorganisms which have been used in producing hyaluronic acid include *S. pyogenes, S. faecalis, S. dysgalactiae, S. zooepidemicus, S. equi, S. equisimilis*, etc.; and they are classified as Lansfield serum group A or C in Bergey's Manual. They are also reported as hemolytic chain-formed cocci having $\beta$ hemolytic action. The processes for producing hyaluronic acid by using a microorganism belonging to the genus Streptococcus are disclosed in, e.g., Japanese Patent Laid-open Publication Nos. 56692/1983 and 500997/1985, Korean Patent Publication No. 92 -9494 and Korean Patent Laid-open Publication No. 87-11252.

In addition, various processes for improving the productivity of hyaluronic acid by employing the microorganisms of Streptococcus have been developed: for example, a process for increasing the productivity of hyaluronic acid by regulating the concentration of phosphate (Korean Patent Publication No. 90-5774); a process using pyruvate, glucosamine, etc.(Japanese Patent Laid-open Publication No. 257901/1987); a process using an aromatic compound containing one or more hydroxy radicals (Japanese Patent Laid-open Publication No. 225491/1989); and a process using amino acids(Japanese Patent Laid-open Publication Nos. 141594/1988 and 289198/1987).

These processes, however, suffer from such deficiencies that hyaluronic acid is produced in a relatively low molecular weight, e.g., ranging from 300 kda to 3,000 kda, and a low yield. As a result, the hyaluronic acid so produced has insufficient moisturizing effect for use, e.g., in cosmetics as well as inferior quality to be used, e.g., in ophthalmic operation, or as a treating agent for arthritis.

SUMMARY OF THE INVENTION

Accordingly, it is a primary object of the present invention to provide a novel mutant microorganism capable of producing high molecular weight hyaluronic acid in a high yield.

Another object of the present invention is to provide a process for producing the high molecular weight hyaluronic acid by utilizing said microorganism.

A further object of the present invention is to provide a medium suitable for culturing a microorganism so as to produce hyaluronic acid in an increased productivity and high molecular weight.

In accordance with one aspect of the present invention, there is provided a novel microorganism belonging to the genus Streptococcus which lacks hyaluronidase activity and hemolytic activity and produces high molecular weight hyaluronic acid.

In accordance with another aspect of the present invention, there is provided a medium suitable for obtaining said high molecular weight hyaluronic acid in a high yield from a strain of the genus Streptococcus, wherein said medium comprises uridine.

BRIEF DESCRIPTION OF THE DRAWINGS

The above and other objects and features of the present invention will become apparent from the following description of preferred embodiments taken in conjunction with the accompanying drawings, in which.

DETAILED DESCRIPTION OF THE INVENTION

Figure 1A:
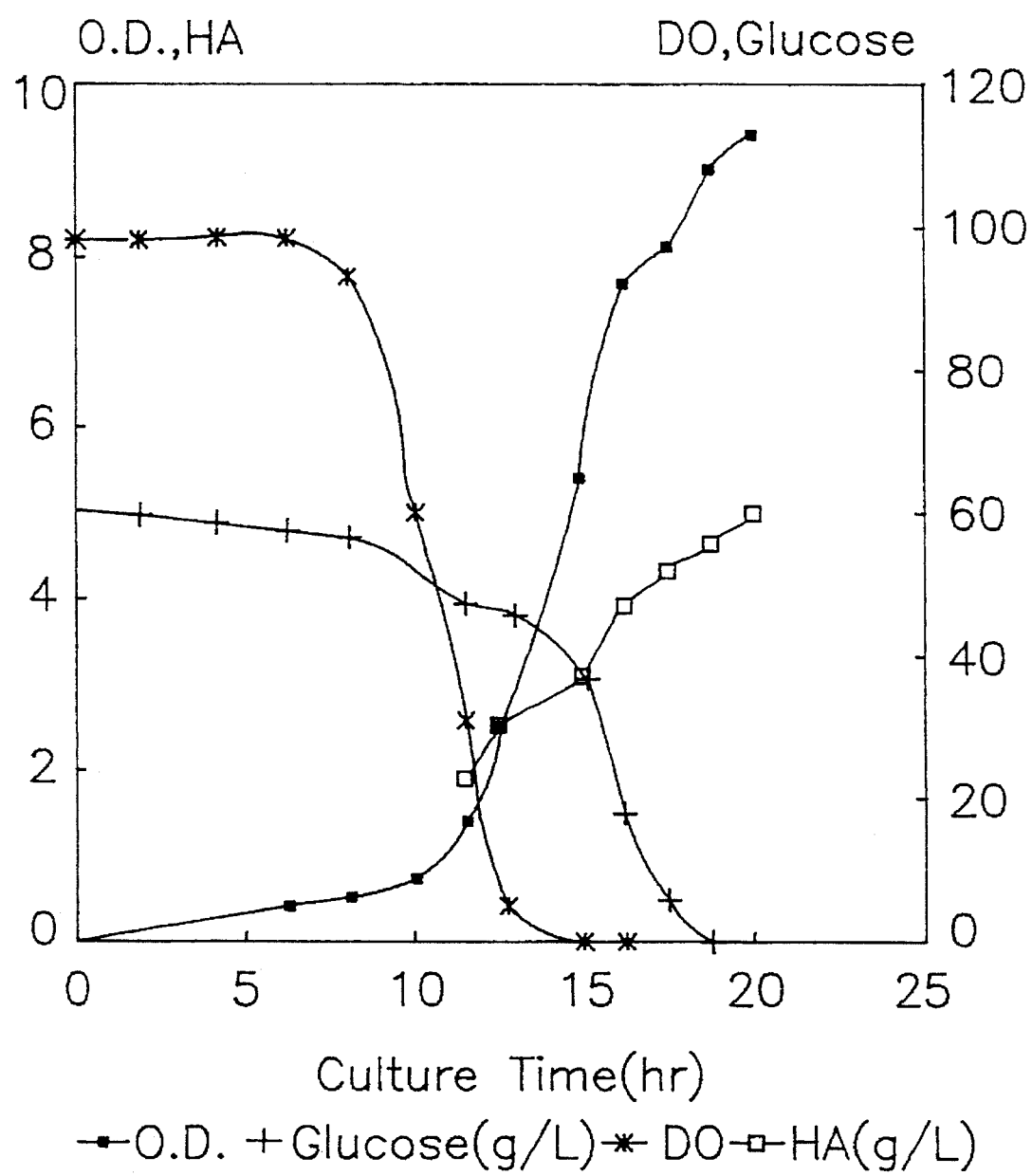
FIGS. 1A and 1B depict the fermentation profiles of *Streptococcus zooepidemicus*(ATCC 35246) and *Streptococcus zooepidemicus* LBF707 of the present invention, respectively.

In accordance with the present invention, a novel microorganism belonging to the genus Streptococcus, which lacks hyaluronidase activity and hemolytic activity and produces high molecular weight hyaluronic acid, is obtained by mutating the known strain of *Streptococcus zooepidemicus*(ATCC 35246). The process of mutagenesis includes at least three times of treatment of the parent microorganism with N-methyl-N' -nitro-N-nitrosoguanidine("NTG"): that is, in accordance with the present invention, mutant strains lacking in hemolytic activity are produced and selected after a first NTG treatment of the known microorganism, followed by a second NTG treatment thereof in order to select strains lacking hyaluronidase which catalyzes the decomposition of hyaluronic acid. Thereafter, the strains so selected are subjected to a third NTG treatment and then incubated on a solid medium to collect rapidly-growing, highly-mucous large colonies as the mutant strains having a superior productivity of hyaluronic acid.

The mutant strains selected according to the above procedure are chosen to lack the hyaluronidase and hemolytic activities and can produce high molecular weight hyaluronic acid having an average molecular weight higher than, e.g., 3,500 kda. One of said mutant strains was designated as "Streptococcus zooepidemicus LBF707" and deposited with Korean Collection for Type Cultures(KCTC) (Address: GERI, KIST, P.O. Box 17, Daeduk Danji, Taejon, 305–606, Republic of Korea) on Jan. 29, 1993 with the accession number of KCTC 0075BP, under the terms of Budapest Treaty on the International Recognition of the Deposit of Microorganism for the Purpose of Patent Procedure.

In general, a medium for incubating a microorganism belonging to the genus Streptococcus comprises a carbon source, a nitrogen source, trace elements such as an inorganic salt, etc. As the carbon source, there may be used starch, glucose, sucrose, galactose, fructose and the like; while glucose is preferred. As the nitrogen source, there may be used ammonium sulfate, ammonium nitrate, sodium nitrate, casamino acid, yeast extract, peptone, tryptone, etc. In addition, there may be added sodium chloride, sodium dihydrogenphosphate, disodium hydrogenphosphate, ferrous sulfate, potassium chloride, magnesium sulfate, etc., if required.

In accordance with the present invention, it has been found that the yield and the molecular weight of hyaluronic acid are respectively increased in the event uridine is added to a medium for incubating a hyaluronic acid-producing microorganism, e.g., the above-mentioned novel microorganism.

Accordingly, the medium of the present invention may preferably comprise, per 1 l of the medium, 10 to 100 g of glucose, 0.5 to 3.0 g of magnesium sulfate, 1.0 to 5.0 g of potassium dihydrogenphosphate, 1.0 to 10.0 g of yeast extract, 10.0 to 20.0 g of yeast peptone and 0.1 to 5.0 g of uridine; and more preferably, 50 g to 70 g of glucose, 0.7 g to 1.5 g of magnesium sulfate, 1.5 g to 2.5 g of potassium dihydrogenphosphate, 4.0 g to 6.0 g of yeast extract, 13.0 g to 17.0 g of yeast peptone and 0.5 g to 1.0 g of uridine.

In addition, it is preferable to carry out an aerobic culturing of the microorganism at a temperature ranging from 33° C. to 38° C. while adjusting the pH of the culture medium to a range from 7.0 to 7.5 and maintaining the aeration rate of 0.1 to 1.0 VVM.

The hyaluronic acid existing in the culture medium after culturing the microorganism normally has the form of a salt, e.g., a sodium salt thereof.

Upon the completion of the culturing of said microorganism, hyaluronic acid existing in the culture medium may be recovered according to a known process for isolating and purifying polysaccharides(Akasaka Hinodedo, *J. Soc. Cosmet. Chem. Japan*, 22, 35–42(1988)).

The amount of hyaluronic acid produced from the mutant microorganism in accordance with the present invention reaches a level ranging from 2.5 to 6.0 g/l; and the average molecular weight thereof is more than 3,500 kda. Quantification of the hyaluronic acid was carried out according to the carbazole method(Z. Dische, *J. Biol. Chem.*, 167, 189(1947)). The molecular weight of the hyaluronic acid was determined by using both high performance liquid chromatography(HPLC) and viscometry. In the method using HPLC, a standard curve was obtained by eluting polyethylene oxide as a standard material, and then hyaluronic acid was eluted under the same condition to obtain its molecular weight with reference to the standard curve(P. Chabreck, *Chromatographia*, 30, 201–204(1990); Narlin B. Beaty, *Anal. Biochem.*, 147, 387–395(1985); Noriko Motohashi, *J. Chrom.*, 299, 508–512(1984)). As for the method using viscometry, the intrinsic viscosity of serially diluted hyaluronic acid was measured by using a viscometer and plotted against the concentration of hyaluronic acid. Limited intrinsic viscosity, which is the intrinsic viscosity of the solution when the concentration of hyaluronic acid is zero, is obtained by extrapolation; and, thereafter, the molecular weight of hyaluronic acid was calculated according to the following equation of Narlin (*Anal. Biochem.*, 147, 387–395(1985)):

$$\text{Limited Intrinsic Viscosity} = 0.000356 \times MW \exp(1.0699)$$

The following Examples are given for the purpose of illustration only and are not intended to limit the scope of the invention.

EXAMPLE 1

Screening of mutant strains
Step 1) Preparation of strains lacking hemolytic activity

*Streptococcus zooepidemicus* (ATCC 35246) was inoculated in 25 ml of Todd-Hewitt liquid medium(Difco, USA, Cat. No. 0492-05-0) and cultured with shaking at 37° C. for 14 hours. Then, 2.5 ml of the resulting culture was inoculated again in 25 ml of Todd-Hewitt medium and cultured with shaking at 37° C. until exponential growth phase was reached. Thereafter, 1 ml of the culture was centrifuged at 4° C.(5,000×g, 5 min.), and the precipitate was collected and washed twice respectively with 1 ml of Tris-maleate buffer(Tris 6 g, pH 6.0, maleic acid 5.8 g, ammonium sulfate 1 g, ferrous sulfate 0.25 mg, magnesium sulfate 0.1 g, calcium nitrate 0.005 g per 1 l). The washed precipitate was suspended in 1 ml of the above buffer solution and then subjected to mutagenesis by adding N-methyl-N'-nitro-N-nitrosoguanidine(NTG) to reach a concentration of 100 to 200 µg/l followed by shaking at 37° C. for 20 to 30 min. or standing for 60 to 120 min.

The resulting NTG treated suspension was centrifuged at 4° C.(5,000×g, 5 min.) and the precipitate was collected and then washed several times with the above buffer solution to remove any residue of NTG. The resulting cell pellets were resuspended in 1 ml of the above buffer solution. 1 ml of the resulting suspension was inoculated in 25 ml of Todd-Hewitt medium and then cultured with shaking at 37° C. for 18 hours to increase the number of viable mutant cells.

The resulting culture was diluted with physical saline; and the diluted solution was plated on a Todd-hewitt agar medium containing 5% blood and incubated at 37° C. for 48 hours. Since colonies having hemolytic activity form clear zones around them, the colonies without clear zones were selected as mutant colonies lacking hemolytic activity.

Step 2) Preparation of strains unable to produce hyaluronidase

The same procedures as described in the above Step 1) were repeated to mutagenize the mutant colonies obtained in the above Step 1) lacking hemolytic activity. The colonies were suspended and diluted with physical saline solution and then plated on Todd-Hewitt agar medium containing 400 µg of hyaluronic acid and 1% of albumin fraction V(Sigma Co., Cat. No. A-2153). After the plate was placed in a humid chamber at 37° C. for 2 to 5 days, about 10 ml of 2N acetate solution was added thereto, and then the plate was allowed to stand for 10 minutes. Hyaluronic acid and albumin were combined in acetate solution to form a precipitate which turned the medium opaque. In case of hyaluronidase-producing colonies, digestion of hyaluronic acid results in clear surroundings. Accordingly, the colonies having opaque surroundings were selected as the mutant strains unable to produce hyaluronidase.

Step 3) Preparation of mutant strains having superior hyaluronic acid productivity The same procedures as described in the above Step 1) were repeated to mutagenize the mutant colonies obtained in the above Step 2). The colonies were diluted with physical saline solution and then plated on a Todd-Hewitt agar medium. The plate was placed in a humid chamber at 37° C. for 48 hours. In this Step 3), *Streptococcus zooepidemicus*(ATCC 35246) was used as a control group. Colonies having higher viscosity and bigger size than those of the control group were selected as mutant strains superior in hyaluronic acid productivity.

Step 4) Preparation of the strains producing high molecular weight hyaluronic acid The following screening procedures were carried out to select a desired strain producing high molecular weight hyaluronic acid from the mutant colonies obtained in the above Step 3).

3 g of Todd-Hewitt medium was dissolved in 150 ml of distilled water and the solution was sterilized at 121° C. for 15 min. Each mutant colony was inoculated separately into the above sterilized medium and incubated at 37° C. for 15 hours as a seed culture. Into a 5 l fermenter was added 3 l of culture medium containing 60 g of glucose, 1.0 g of magnesium sulfate, 2.0 g of potassium dihydrogenphosphate, 5.0 g of yeast extract, 15.0 g of yeast peptone and 0.75 g of uridine per 1 l of medium, and the medium was steam-sterilized at 121° C. for 20 min. Then, 150 ml of the above seed culture was added thereto, and cultured while maintaining the pH of 7.1 and temperature of 35° C. with aeration rate of 0.5 vvm for 24 hours.

The culture was filtered through a 0.45 μm filter. The filtrate was subjected to high performance liquid chromatography, and then the mutant strain producing hyaluronic acid having molecular weight much higher than that of hyaluronic acid produced by *Streptococcus zooepidemicus* ATCC 35246 was obtained by selecting the strain which produced hyaluronic acid which was eluted fastest. It was determined the hyaluronic acid produced by the present mutant strain has an average molecular weight of more than 3,500 kda.

Step 5) Bacteriological properties of the mutant strain

The mutant strain obtained in the present invention exhibits the following bacteriological properties:

Gram stain: positive growth at 10° C.: negative growth at 45° C.: negative growth in 6.5% saline: negative growth at pH 9.6: negative growth in 40% bile: negative arginine decomposability: positive hippurate decomposability: negative esculin decomposability: negative bacitracin resistance: negative saccharide decomposability glucose, maltose, sucrose, sorbitol, lactose: positive mannitol, glycerine, trehalose: negative As can be seen from the above, the novel mutant strain has the same properties as those of *Streptococcus zooepidemicus* described in Bergey's Manual of Determinative Bacteriology(1974), except for the lack of hemolytic activity and hyaluronidase production; and designated as *Streptococcus Zooepidemicus* LBF707.

Comparative Example 1

Comparison of yield for hyaluronic acid

Figure 1B:
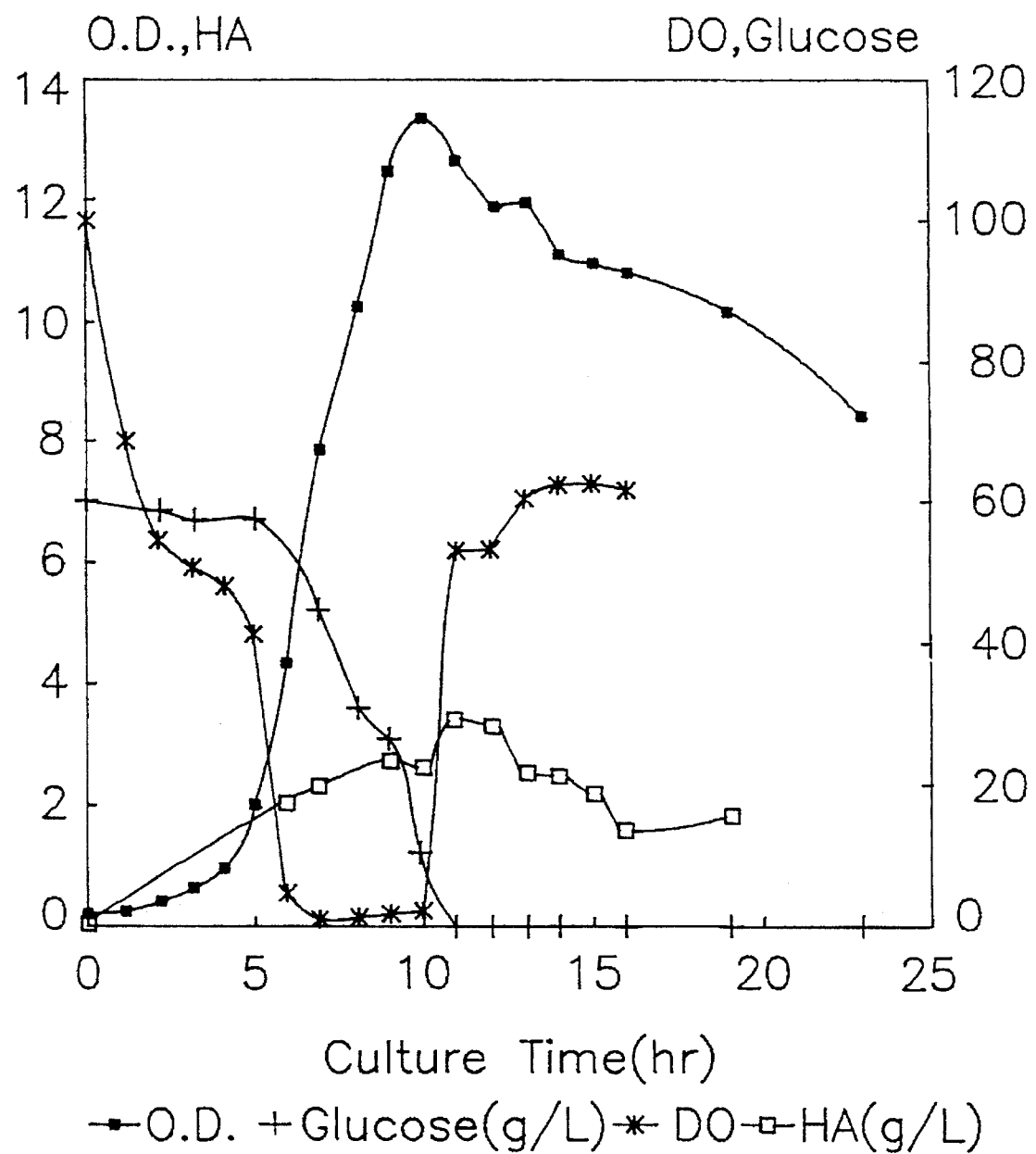

The yields of hyaluronic acid produced by *Streptococcus zooepidemicus* LBF707 obtained in Step 4) of Example 1 and *Streptococcus zooepidemicus*(ATCC 35246) were compared. As can be seen from FIG. 1, it was determined that the yield of hyaluronic acid per unit volume of fermentation in case of using the novel mutant microorganism is higher by about 20% than that of using *Streptococcus zooepidemicus*(ATCC 35246).

Comparative Example 2

Comparison of molecular weight

Figure 2:
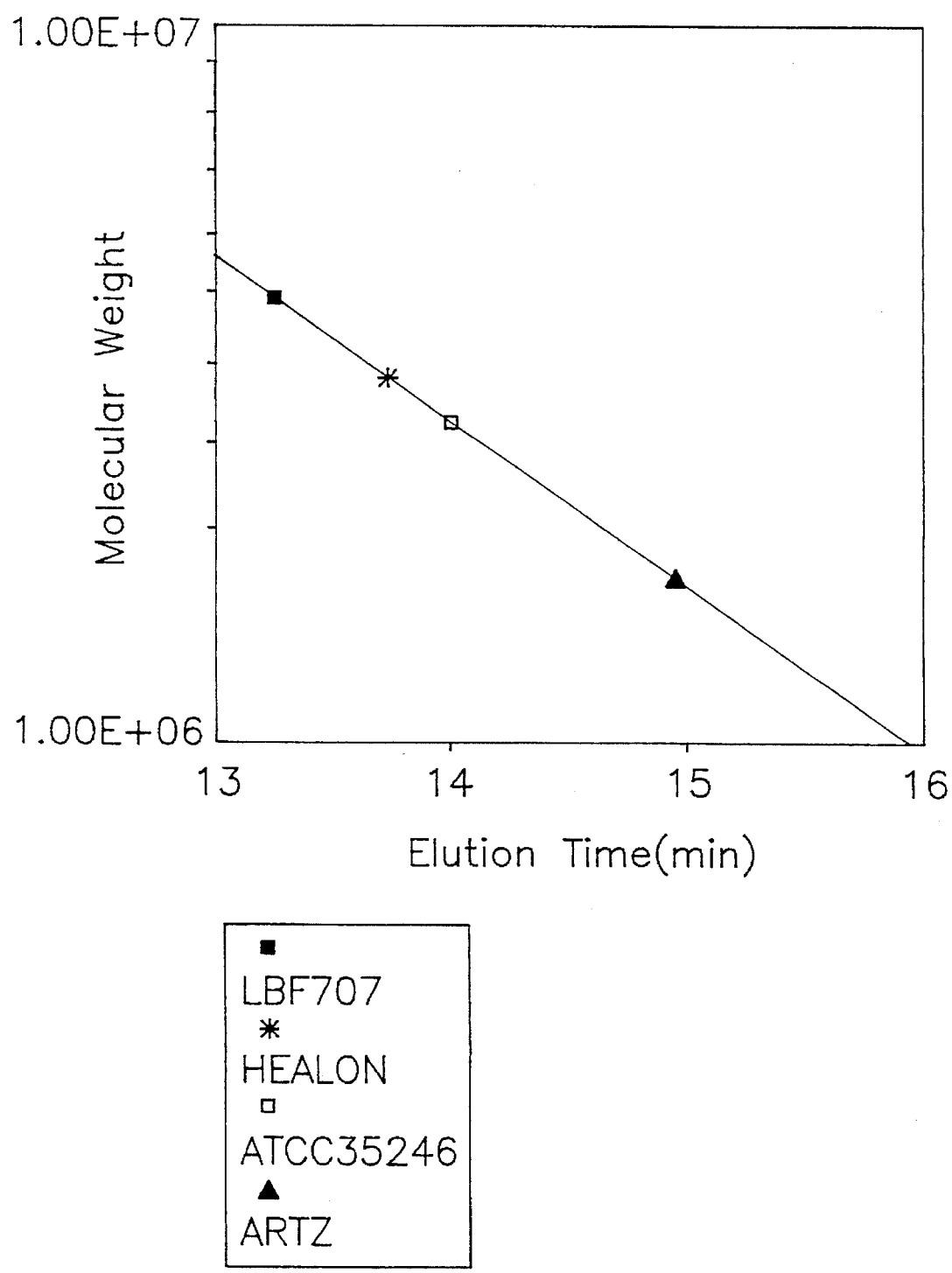
FIG. 2 shows the molecular weight of hyaluronic acid obtained in accordance with the present invention as compared with those of other hyaluronic acid which is produced by using *S. zooepidemicus*(ATCC 35246) and commercially available products.

The molecular weights of hyaluronic acids obtained respectively from the culture of the above mutant microorganism and *Streptococcus zooepidemicus*(ATCC 35246) were compared with those of commercially available hyaluronic acid products extracted from animal tissues, for example, HEALON (Pharmacia AB, Sweden, lot No. RH41401) and ARTZ(Biochemical Industry Inc., Japan) by using high performance liquid chromatography. As can be seen from FIG. 2, the hyaluronic acid produced by the mutant strain of the present invention, *Streptococcus zooepidemicus* LBF707, has the highest molecular weight.

Figure 3:
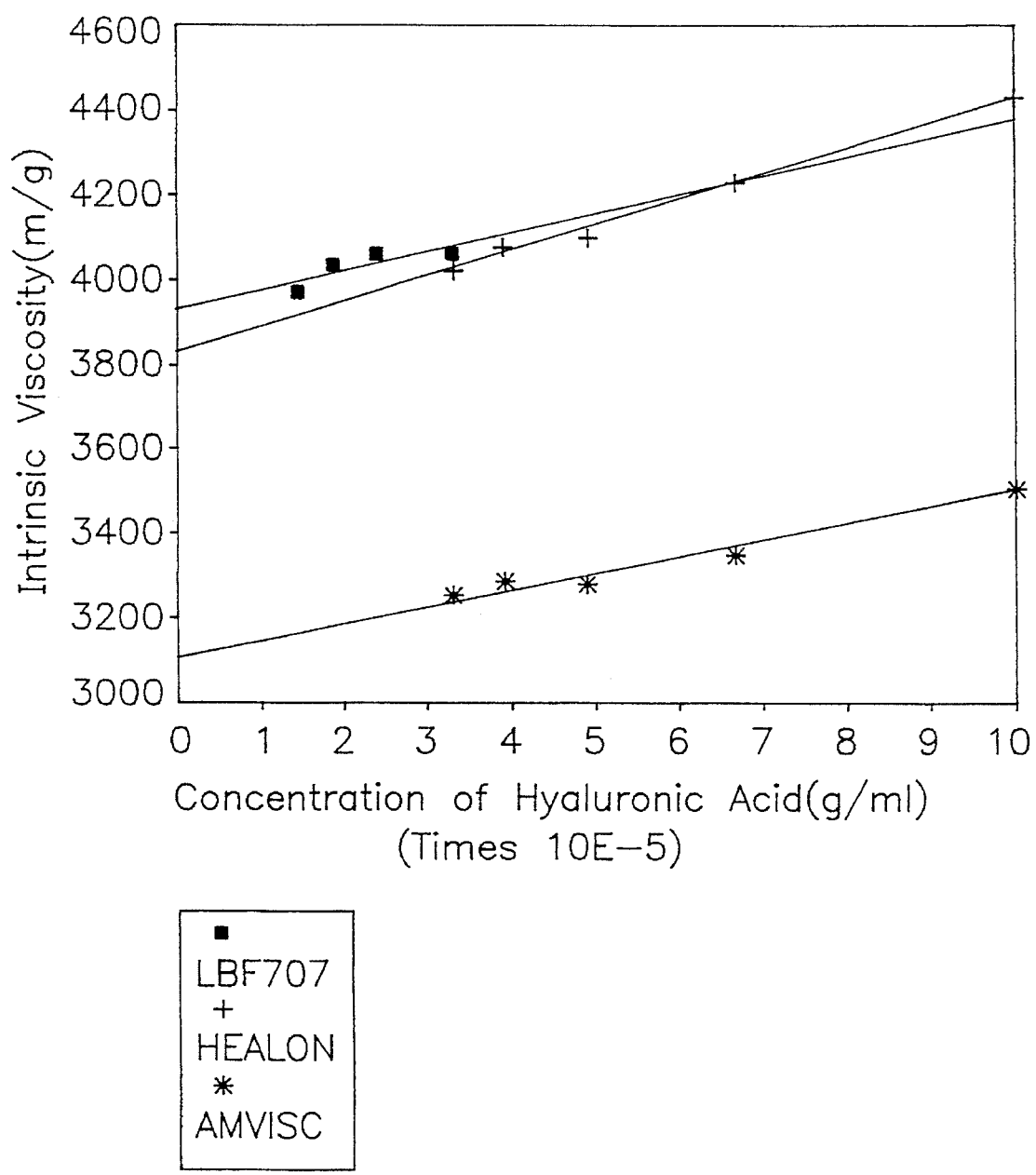
FIG. 3 describes the change of intrinsic viscosity with respect to the concentration of the hyaluronic acid obtained by using the inventive process in comparison with that of hyaluronic acid produced by the prior art methods.

In addition, the viscosity of hyaluronic acid produced by using *Streptococcus zooepidemicus* LBF707 and of commercially available hyaluronic acid products extracted from animal tissues, i.e., HEALON and AMVISC (Johnson & Johnson, USA) were determined by employing a viscometer. As shown in FIG. 3, the hyaluronic acid produced by the mutant strain of the present invention has the highest limited intrinsic viscosity. The molecular weight of each of hyaluronic acid products was further calculated by using Narlin's equation from its limited intrinsic viscosity value, respectively. As a result, the average molecular weight of hyaluronic acid produced by *Streptococcus zooepidemicus* LBF707 was 3,800 kda, that of HEALON was 3,700 kda and that of AMVISC was 3,100 kda.

EXAMPLE 2

Culture of microorganisms in a medium comprising uridine

Into each of five 5 l fermenters were added 3 l of culture medium containing 60 g of glucose, 1.0 g of magnesium sulfate, 2.0 g of potassium dihydrogenphosphate, 5.0 g of yeast extract and 15.0 g of yeast peptone per 1 l of medium. Uridine was added to the fermenters in an amount of 0, 0.5, 0.75, 1.0 and 2.0 g per 1 l of medium, respectively. The media were steamsterilized at 121° C. for 20 min.; and then 150 ml of the seed culture of *Streptococcus zooepidemicus* ATCC 35246 was added thereto and cultured for 24 hours maintaining the pH of 7.2, temperature of 35° C. with aeration rate of 0.5 vvm. Thereafter, the concentration of hyaluronic acid in each culture medium was determined; and the results are shown in Table 1 below.

TABLE 1

| Yield of hyaluronic acid according to the concentration of uridine | | | | | |
|---|---|---|---|---|---|
| Concentration of uridine in | 0 (control) | 0.5 | 0.75 | 1.0 | 2.0 |

TABLE 1-continued

Yield of hyaluronic acid according to the concentration of uridine

| medium (g/l) | | | | | |
|---|---|---|---|---|---|
| Yield of hyaluronic acid (g/l) | 3.5 | 4.1 | 4.8 | 4.8 | 5.0 |

As can be seen from the above Table 1, addition of uridine increases the production of hyaluronic acid.

Comparative Example 3

Comparison of molecular weight of hyaluronic acid produced in the medium with or without uridine The same culture procedures as described in Example 2 were repeated by using the same medium composition and culture condition with the exception that the concentration of uridine was fixed at 0.75 g/l. When the culture was completed, the concentration of hyaluronic acid in the culture medium was determined to be about 4.8 g/l.

Figure 4:
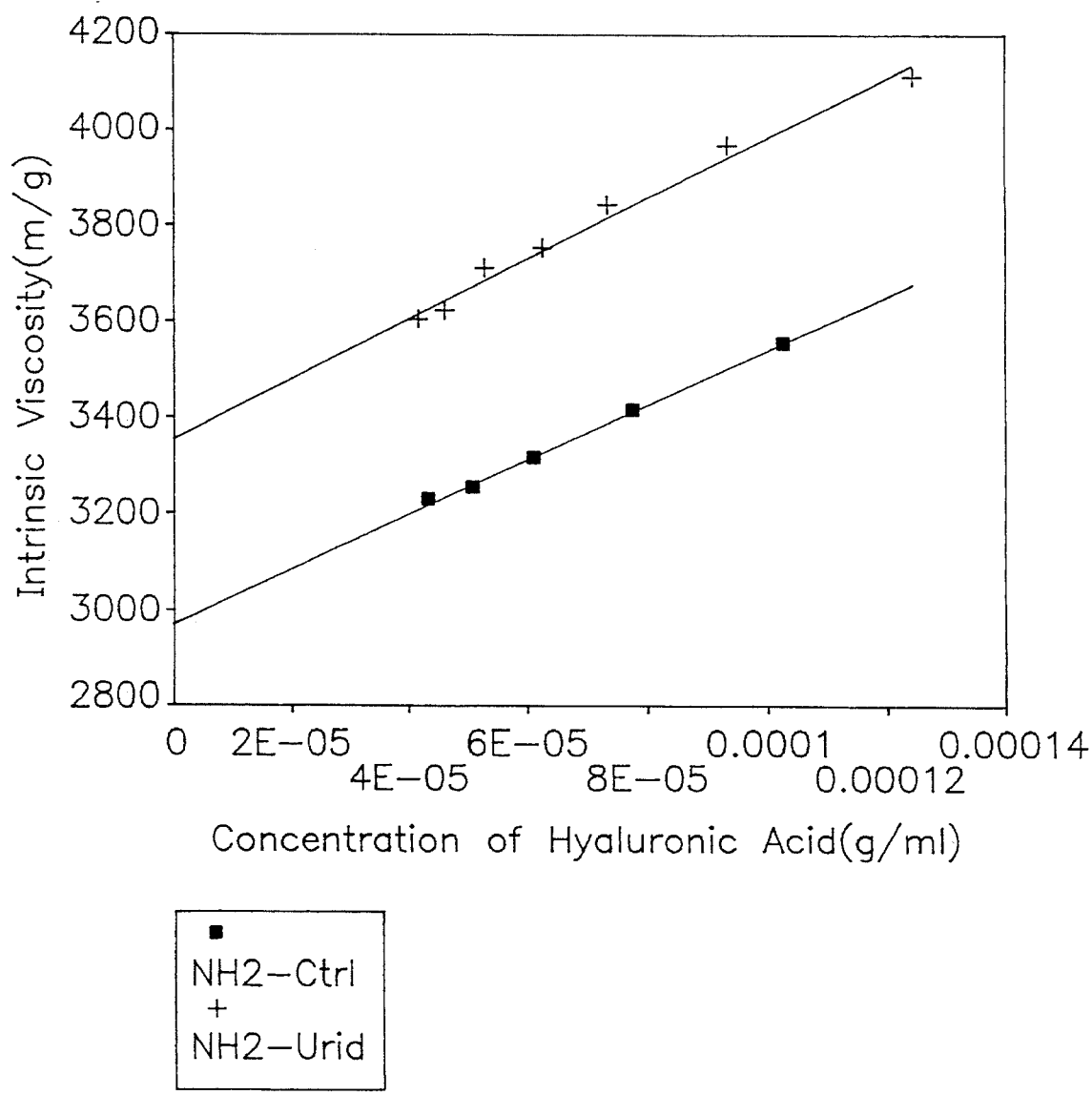
FIG. 4 shows the effect of uridine on the intrinsic viscosity of hyaluronic acid.

Molecular weight of hyaluronic acid obtained in the present Comparative Example were compared with that of the hyaluronic acid used as the control in Example 2. FIG. 4 shows the variation of intrinsic viscosity with the concentration (and the limited intrinsic viscosity) of hyaluronic acid produced in the medium with or without uridine. In FIG. 4, NH2-Ctrl represents the hyaluronic acid obtained in the medium without uridine(Example 2, control group) and NH2-Urid represents the hyaluronic acid obtained in the medium with uridine(the present Comparative Example, experimental group). The limited intrinsic viscosity value of the control group was about 3,000 ml/g and that of experimental group was about 3,400 ml/g. The molecular weights of the control group and the experimental group were calculated by substituting the above limited intrinsic viscosity values into the Narlin's equation previously described, and they were about 3,000 kda for control group and about 3,300 kda for experimental group. This result shows that addition of uridine to a culture medium increases the molecular weight of hyaluronic acid.

EXAMPLE 3

Batch culture of the novel microorganism

Into a 5 l fermenter was added 3 l of culture medium containing 60 g of glucose, 1.0 g of magnesium sulfate, 2.0 g of potassium dihydrogenphosphate, 5.0 g of yeast extract, 15.0 g of yeast peptone and 0.75 g of uridine per 1 l of medium.

The medium was steam-sterilized at 121° C. for 20 min., and then 150 ml of the seed culture solution of *Streptococcus zooepidemicus* LBF707 was added thereto and cultured for 24 hours maintaining the pH of 7.1 to 7.3, temperature of 35° to 38° C. with aeration rate of 0.1 to 1.0 vvm. When the culture was completed, the concentration of hyaluronic acid in the culture medium was 6.0 g/l and average molecular weight of hyaluronic acid was about 3,500 kda.

EXAMPLE 4

Fed-batch culture of the novel microorganism

The culturing was carried out initially with the same medium composition and condition as of Example 3 except that the concentration of glucose was 40 g/l. After 12 to 18 hours, the culture was converted to a fed-batch culture in which glucose was added so as to maintain the concentration of glucose in the medium below 10 g/l. The culturing was carried out for 24 to 36 hours until the concentration of hyaluronic acid did not increase any further. When the culturing was completed, the concentration of hyaluronic acid in the culture solution was found to be 5.0 g/l and the average molecular weight of hyaluronic acid was about 3,500 kda.

While the invention has been described with respect to the above specific embodiments, it should be recognized that various modifications and changes which may be apparent to those skilled in the art to which the invention pertains may be made and also fall within the scope of the invention as defined by the claims that follow.

What is claimed is:

1. A strain of *Streptococcus zooepidemicus* having all the identifying characteristics of *Streptococcus zooepidemicus* LBF707(KCTC 0075BP).

2. The strain of claim 1, which is *Streptococcus zooepidemicus* LBF707(KCTC 0075BP).

3. The strain of claim 1, which is prepared by a process which comprises:

mutagenizing *Streptococcus zooepidemicus* ATCC 35246 with N-methyl-N'-nitro-N-nitrosoguanidine at least three times to thereby produce mutant strains; and selecting therefrom a mutant strain that lacks hemolytic activity and hyaluronidase activity and forms a colony having a higher viscosity and a bigger size than the viscosity and size of a colony formed by *Streptococcus zooepidemicus* ATCC 35246.

* * * * *